United States Patent
Kriz et al.

(10) Patent No.: US 6,858,421 B2
(45) Date of Patent: Feb. 22, 2005

(54) CYTOSOLIC PHOSPHOLIPASE $A_2$-BETA ENZYMES

(75) Inventors: Ronald Kriz, Hudson, MA (US); Chuanzheng Song, Warren, NJ (US)

(73) Assignee: Genetics Institute, L.L.C., Cambridge, MA (US)

( * ) Notice: Subject to any disclaimer, the term of this patent is extended or adjusted under 35 U.S.C. 154(b) by 103 days.

(21) Appl. No.: 10/266,388

(22) Filed: Oct. 7, 2002

(65) Prior Publication Data

US 2003/0124702 A1 Jul. 3, 2003

Related U.S. Application Data

(62) Division of application No. 09/895,547, filed on Jun. 29, 2001, now Pat. No. 6,482,625, which is a division of application No. 09/460,145, filed on Dec. 13, 1999, now Pat. No. 6,287,838, which is a continuation of application No. 08/788,975, filed on Jan. 24, 1997, now abandoned.

(51) Int. Cl.[7] .......................... C12N 9/16; A01N 25/00; C12Q 1/34; C07K 1/00; C07H 21/04
(52) U.S. Cl. ............................ 435/196; 435/4; 435/6; 435/18; 536/23.2; 530/350; 517/789
(58) Field of Search ............................ 435/196, 6, 440, 435/71.1, 252.3, 320.1, 18, 4; 536/23.2; 514/789; 530/350

(56) References Cited

U.S. PATENT DOCUMENTS

| | | |
|---|---|---|
| 4,239,780 A | 12/1980 | Wallach |
| 4,917,826 A | 4/1990 | Johnson et al. |
| 5,279,957 A | 1/1994 | Gross |
| 5,322,776 A | 6/1994 | Knopf et al. |
| 5,328,842 A | 7/1994 | Chiou et al. |
| 5,354,677 A | 10/1994 | Knopf et al. |
| 5,356,787 A | 10/1994 | Gross |
| 5,466,595 A | 11/1995 | Jones et al. |
| 5,527,698 A | 6/1996 | Knopf et al. |
| 5,554,511 A | 9/1996 | Jones et al. |
| 5,589,170 A | 12/1996 | Jones et al. |
| 5,593,878 A | 1/1997 | Knopf et al. |
| 5,840,511 A | 11/1998 | Jones et al. |
| 5,976,854 A | 11/1999 | Jones et al. |
| 6,274,140 B1 | 8/2001 | Jones et al. |

OTHER PUBLICATIONS

Aarmsman, Anton J. et al. (1998) "Immunoaffinity Purification, Partial Sequence, and Subcellular Localization of Rat Livers Phospholipase $A_2$." *Journal of Biological Chemistry*, 264(17): 10008–10014.

Ackerman, Elizabeth J. et al. (1994) "$Ca^{2+}$—independent Cytosolic Phospholipase $A_2$ from Macrophage–like P388D1 Cells." *The Journal of Biological Chemistry*, 269 (12): 9227–9233.

Ackerman, Elizabeth J. et al. (1993) "Direct Effect of Hyaluronan on Cell Behavior." *FASEB Journal*, 7 (7): 1237–1241.

Angle, Marlene J. et al. (1998) "Selective Hydrolysis of Ether–containing Glycerophospholipids by Phospholipase $A_2$ in Rabbit Lung." *Biochimica Acta*, 962: 234–240.

(List continued on next page.)

Primary Examiner—P. Achutamurthy
Assistant Examiner—Yong D. Pak
(74) Attorney, Agent, or Firm—Finnegan, Henderson, Farabow, Garrett & Dunner, LLP

(57) ABSTRACT

The invention provides a novel calcium-independent cytosolic phospholipase $A_2$-Beta enzyme, polynucleotides encoding such enzyme and methods for screening unknown compounds for anti-inflammatory activity mediated by the arachidonic acid cascade.

13 Claims, 2 Drawing Sheets

OTHER PUBLICATIONS

Cao, Y.Z. et al. (1987) "The purification and characterization of a phospholipase A in hamster heart cytosol for the hydrolysis of phosphatidylcholine"*J. Biol. Chem.*, 262 (35):16927–16935.

Clark, J. D. (1991) "A Novel Arachidonic Acid–selective Cytosolic $PLA_2$ Contains a $Ca^2+$—dependent Translocation Domain with Homology to PKC and GAP." *Cell*, 65:1043–51.

de Carvalho, M.S. et al. (1993) "The 85–kDa, Arachidonic Acid–specific Phospholipase $A_2$ is Expressed as an Activated Phosphoprotein in Sf9 cells." *Arch. Biochem. Biophys.*, 306 (2): 534–540.

Dennis, E. A. (1994) "Diversity of Group Types, Regulation, and Function of Phospholipase $A_2$." *J. Biol. Chem.*, 269 (18): 13057–13060.

Ford, David A. et al. (1991) "The Rapid and Reversible Activation of a Calcium–independent Plasmalogen–selective Phospholipase $A_2$ During Myocardial Ischemia." *Journal of Clinical Investigation*, 88: 331–335.

Gassama–Diagne, Ama et al. (1992) "Substrate specificity of phospholipase B from guinea pig intestine. A glycerol ester lipase with broad specificity." *J. Biol. Chem.* 267 (19):13418–13424.

Gassama–Diagne, Ama et al. (1989) "Purification of a New, Calcium–independent, High Molecular Weight Phospholipase $A_2$/Lysophospholipase (Phospholipase B) from Guinea Pig Intestinal Brush–border Membrane." *The Journal of Biological Chemistry*, 264 (16): 9470–9475.

Gross, Richard W. et al. (1993) "Rat and Human Pancreatic Islet Cells Contain a Calcium Ion Independent Phospholipase $A_2$ Activity Selective for Hydrolysis of Arachidonate Which is Stimulated by Adenosine Triphosphate and Is Specifically Localize to Islet β–cells." *Biochemistry*, (32): 327–336.

Gross, R. (1991) TCM, 2: 115.

Han, J. H. et al. (1987) "Isolation of Full–length Putative Rat Lysophospholipase cDNA using improved methods for mRNA isolation and cDNA cloning." *Biochemistry*, 26:1617–1625.

Hazen, Stanley L. et al. (1993) "Isolation of a Human Myocardial Cytosolic Phospholipase $A_2$ Isoform: Fast Atom Bombardment Mass Spectroscopic and Reverse–Phase High Pressure Liquid Chromatography Identification of Choline and Ethanolamine Glycerophospholipid Substrates." *Journal of Clinical Investigation*, 91: 2513–2522.

Hazen, Stanley L. et al. (1991) "ATP–dependent Regulation of Rabbit Myocardial Cytosolic Calcium–independent Phospholipase $A_2$." *The Journal of Biological Chemistry*, 266(22): 14526–14534.

Hazen, Stanley L. et al. (1990) "Purification and Characterization of Canine Myocardial Cytosolic Phospholipase $A_2$. A Calcium–Independent Phospholipase with absolute f1–2 regiospecificity for diradyl glycerophospholipids." *The Journal of Biological Chemistry*, 265 (18): 10622–10630.

Hazen, Stanley L. et al. (1993) "The Specific Association of a Phosphofructokinase Isoform with Myocardial Calcium–independent Phospholipase $A_2$. Implications for the Coordinated Regulation of Phospholipolysis and Glycolysis." *The Journal of Biological Chemistry*, 268 (13): 9892–9900.

Hazen, Stanley L. et al. (1991) "Activation of Membrane–associated Phospholipase $A_2$. During Rabbit Myocardial Ischemia Which is Highly Selective for Plasmalogen Substrate." *The Journal of Biological Chemistry*, 266 (9) 5629–5633.

Hazen, Stanley L. et al. (1991) "Purification and Characterization of Cytosolic Phospholipase $A_2$ Activities from Canine Myocardium and Sheep Platelets." *Methods in Enzymology*, 197: 400–411.

Hazen, Stanley L. et al. (1992) "Identification and Characterization of Human Myocardial Phospholipase $A_2$ From Transplant Recipients Suffering from End–Stage Ischemic Heart Disease." *Circulation Research*, 70: 486–495.

Hazen, Stanley L. et al. (1991) "Suicide Inhibition of Canine Myocardial Cytosolic Calcium–independent Phospholipase $A_2$. Mechansim–based Discrimination Between Calcium–dependent and –independent Phospholipids." *The Journal of Biological Chemistry*, 266 (11): 7227–7232.

Hillier et al. (1995) EMBL Sequence Data Library: Accession No. H10676.

Hirashima, Yutaka et al. (1992) "Identification and Purification of Calcium–independent Phospholipase $A_2$ from Bovine Brain Cytosol." *The Journal of Neurochemistry*, 59 (2): 708–714.

Kanada, A. et al. (1989) "The Primary Structure of a Membrane–associate Phospholipase $A_2$ from Human Spleen." *Biochem. Biophys. Res. Comm.*, 163:42–48.

Kaufman, R.J. et al. (1991) "Improved Vectors for Stable Expression of Foreign Genes In Mammalian Cells By The Use of the Untranslated Leader Sequence From EMC Virus." *Nucleic Acids Research*, 19: 4485–4490.

Kaufman, R.J. (1990) "Selection and Coamplification of Heterologous Genes in Mammalian Cells." *Methods in Enzymol.* 185: 537–566.

Kramer, R.M. et al. (1989) "Structure and Properties of a human non–pancreatic phospholipase $A_2$." *J. Biol. Chem.*, 264:5768–5775.

Lehman, John. J. et al. (1993) "Arachidonic Acid Release from Aortic Smooth Muscle Cells Induced by [$Arg^8$] Vasopressin is Largely Mediated by Calcium–independent Phospholipase $A_2$." *The Journal of Biological Chemistry*, 268 (28):20713–20716.

Leslie, C.C. et al. (1988) "Properties and Purification of an arachidonoyl–hydrolyzing phospholipase $A_2$ from a macrophage cell line, RAW 264.7" *Biochim. Biophys. Acta*, 963:476–492.

Loeb, Lori A. et al. (1993) "Identification and Purification of Sheep Platelet Phospholipase $A_2$ Isoforms. Activation by Physiologic Concentrations of Calcium Ion." *The Journal of Biological Chemistry*, 261 (23): 10467–10470.

Nijssen, J. G. et al. (1986) "Identification of a Calcium–independent Phospholipase $A_2$ in Rat Lung Cytosol and Differentiation from Acetylhydrolase for 1–alkyl–sn–glycero–3–phosphocoline (PAF–acether)." *Biochimica et Biophysical Acta*, 876: 611–618.

Pierik, Antonio J. et al. (1988) "Calcium–independent phospholipase $A_2$ in rat tissue cytosols." *Biochimica et Biophysica Acta*, 962: 345–353.

Ramanadham, S. et al. (1993) "Inhibition of Arachidonate Release by Secretagogue–Stimulated Pancreatic Islets Suppresses Both Insulin Secretion and the Rise in β–Cell Cytosolic Calcium Ion Concentration." *Biochemistry*, 32: 337–346.

Ramanadham, S. et al. (1994) "Characterization of an ATP–stimulatable $Ca^{2+}$—Independent Phospholipase $A_2$ from Clonal Insulin–Secreting HIT Cells and Rat Pancreatic Islets: a Possible Molecular Component of the β–cell Fuel Sensor." *Biochemistry*, 33(23):7442–7452.

Ross, Merrick I. et al, (1985) "Phospholipase Activities of the $P338D_1$ Macrophage–like Cell Line[1]." *Archives of Biochemistry and Biophysics*, 238 (1): 247–258.

Saito, Kunihiko et al. (1991) "Phospholipase B from *Pencillium notatum*." *Methods in Enzymology*, 197: 446–456.

Seilhamer, J.J. et al. (1989) "Cloning and Recombinant Expression of Phospholipase $A_2$ Present in Rheumatoid Arthiritic Synovial Fluid." *J. Biol. Chem.*, 264 (10): 5335–5338.

Sharp, J.D. et al. (1991) "Molecular Cloning and Expression of Human $Ca^{2+}$—sensitive Cytosolic Phospholipase $A_2$." *J. Biol. Chem.*, 266 (23): 14850–14853.

Song, Chuanzheng et al. (1999) "Molecular Characterization of Cytosolic Phospholipase $A_2$–β." *The Journal of Biological Chemistry*, 274 (24): 1763–1767.

Street, I.P. et al. (1993) "Slow– and Tight–Binding Inhibitors of the 85–kDa Human Phospholipase A2." *Biochemistry*, 32: 5935–5940.

Tang, J. et al. (1997) "A Novel Cytosolic Calcium–independent Phospholipase $A_2$ Contains Eight Ankyrin Motifs." *J. Biol. Chem.*, 272 (13): 8567–8575.

Ueda, Hiroshi et al. (1993) "The Presence of $Ca^{2+}$—Independent Phospholipase $A_1$ Highly Specific For Phosphatidylinositol In Bovine Brain." *Biochemical and Biophysical Research Communications*, 195(3): 1272–1279.

Ulevitch, Richard J. et al. (1988) "Solubilization, Purification, and Characterization of a Membrane–bound Phospholipase $A_2$ from the P388D1 Macrophage–like Cell Line." *The Journal of Biological Chemistry*, 263 (7): 3079–3085.

Williams, Roger Lee et al. (1987) "The Crystal Structure if Ribonuclease B at 2.5—A resolution." *The Journal of Biological Chemistry*, 262 (33): 16020–16031.

Wolf, Robert A. et al. (1985) "Identification of Neutral Active Phospholipase C Which Hydrolyzes Choline Glycerophospholipids and Plasmalogen Selective Phospholipase $A_2$ in Canine Myocardium," *The Journal of Biological Chemistry*, 260 (12): 7295–7303.

Yost, Robert W. et al. (1991) "Yeast Mitochondria (*Saccharomyces cerevisiae*) Contain $Ca^{2+}$—Independent Phospholipase $A_1$ and $A_2$ Activities: Effect of Respiratory State" *Biochemistry International*, 24 (2): 199–208.

Zupan, Lori A. et al. (1992) "Cloning and Expression of a Human 14–3–3 Protein Mediating Phospholipolysis." *The Journal of Biological Chemistry*, 267 (13): 8707–8710.

Zupan, Lori A. et al. (1993) "Structural Determinants of Haloenol Lactone–Mediated Suicide Inhibitors of Canine Myocardial Calcium–Independent Phospholipase $A_2$." *J. Med. Chem.*, 36: 95–100.

Zupan, Lori A. et al. (1991) "Calcium Is Sufficient But Not Necessary For Activation of Sheep Platelet Cytosolic Phospholipase $A_2$." *FEBS Letters*, 284 (1): 27–30.

GenBank Accession No. W92213, e14h11.rl Soares_fetal heart_NbHH19W Homo sapiens cDNA clone IMAGE:359013 5' similar to PIR:A39329–A39329 phospholipase $A_2$; mRNA sequence.

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
       (A) LENGTH: 4183 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 1:

```
CTCCTACAAC TCAATATAAA AACATAAACC CAGCCGGGTG CAGTGGCTCA TGCCTGTAAT     60
CCCAACACTT TGGAAAGGCC AAGGTGGGTG GATCACCTGA GGTCAGGAGT TCAAGACCAG    120
CCTGGCCAAC ATGGTAAGAC CCGTCTCTAC TAAAAATACA AAAATTAGCC AGTGTAGTGG    180
TGGGCACCTG TAATCCAGCT ACTCAGGAGG CTGGGGCAGG AGAATCACTT GAACCTGGGA    240
GGCGGAGGTT GCAGTGAGCC GAGATTGCAC CATTGCACTC CTGCTTGGGT GACAGAGCGA    300
GACTCCATCT CAAAAAAAAA AAAGATAAAC CCAATTTTAA AATGGGCAAA AGACCTGAAT    360
AGGCAAACCT CCAAAGAAAA TATGTGCATG AAAAGATGCT TAACATCATT TGTCATCAAA    420
TGGTTAGGAA ATTGCAAATC AAAACCACAG TGAGATACCT CTTCAAACTT ACTAGGATGG    480
CTATAATCAA AAAGATAAAC AACAACAAGT ATTAGAGATG ATGTGGAGAA ACTAGAACCC    540
TCATATATGC TGGTGGGAAT GTAAAATGGT GCAGCCACTT TGGAAAACTG TCTGGCATTT    600
CTTCAAAAAG TAACATAGAG TTACTGTATG ACCCAGCAAT TCCACTGCTA GTGTGTATCC    660
AAGAGAAATG AAAACGTGTC CACACAAAAA GTTGGACACA AATGTTCACG GCAGCATTGT    720
TTATAATAGC CAAAAAATAG AAACACCCAA ATGTCCATCA ACTGATTTAA TGAGTAAAGA    780
TAATGAGATA TGTCTATACA ATAGATTATT ATTTGGCAAT AAAAAGGAAT AAAGTTCTGG    840
TTGGGCATGG TGGCTCACAC CTGTAATCCC AGCACTTTGA GAGGCTGAGG TGGGAAGACT    900
GCTTAAGCCA GAAGTTCAAG ACCAGCCCAG ACAACAAAGC AAGACCTTAT CTCTACAGAC    960
TTTCTAAAAA TTAGCCAGGT GTGGCTGGGT GTGGTGGCTC ACGCCTGTAG TCCCAGCACA   1020
TTGGAGGCA TAGGCGGGCG GATCACGAGG TCAGGAGATG GAGACCATCC TGGTTAACAC    1080
GGCGAAACCC CGTCTCTACT AAAAATACAA AAAATTAGCT GGGCGTGGTG GCGGGCGCCT   1140
GTAGTCCCAG CTACTCGGGA AGCCGAGGCA GGAGAATGGC GTGAACCTGG GAGGTGGAGC   1200
TCGCAGTGAG CCGAGATCGC GCCACTGCAC TCCAGCCTGG GGACAGAGT GAGACTCCCA    1260
TCCCAAAGAA AAAAAAAATT AGCCGGGTGT GGTGGTACAT GCCAGTAGTC CCAGCTACCT   1320
GGGAGGCCAA GGCAGGAGGA CTGCTTGAAT CCAGGAAGTT GAGGCTGCAG TGAGCGATGA   1380
TGGCACCACT GCACTTCAAC CTAGACAAGG TCGACGCGGC CNNGAATTAG CGNCCGCGTC   1440
GANNGATGGG CCTGGGGTTC AGGATTAGGC CTTGAGGCAC TGCTCCAGCC TCCTTTGTGG   1500
CCCCTGTCAC CCTTGGCTTC ATCGGCCCGT AGCAGGTCTC CCCTCTCCCA CCTCTGCAGG   1560
CAGAGGTGTC CAGGACCTGC CTGCTCACGG TTCGTGTCCT GCAGGCCCAT CGCCTACCCT   1620
CTAAGGACCT AGTGACCCCC TCTGACTGCT ACGTGACTCT CTGGCTGCCC ACGGCCTGCA   1680
GCCACAGGCT CCAGACACGC ACGGTCAAGA ACAGCAGTAG CCCTGTCTGG AACCAGAGCT   1740
TTCACTTCAG GATCCACAGG CAGCTCAAGA ATGTCATGGA ACTGAAAGTC TTTGACCAGG   1800
```

-continued

```
ACCTGGTGAC CGGAGATGAC CCTGTGTTGT CAGTACTGTT TGATGCGGGG ACTCTGCGGG      1860

CTGGGGAGTT CCGGCGCGAG AGCTTCTCAC TGAGCCCTCA GGGTGAGGGG CGCCTGGAAG      1920

TTGAATTTCG CCTGCAGAGT CTGGCTGACC GTGGCGAGTG GCTCGTCAGC AATGGCGTTC      1980

TGGTGGCCCG GGAGCTCTCC TGCTTGCACG TTCAACTGGA GGAGACAGGA GACCAGAAGT      2040

CCTCAGAGCA CAGAGTTCAG CTTGTGGTTC CTGGGTCCTG TGAGGGTCCG CAGGAGGCCT      2100

CTGTGGGCAC TGGCACCTTC CGCTTCCACT GCCCAGCCTG CTGGGAGCAG GAGCTGAGTA      2160

TTCGCCTGCA GGATGCCCCC GAGGAGCAAC TAAAGGCGCC ACTGAGTGCC CTGCCCTCTG      2220

GTCAAGTGGT GAGGCTTGTC TTCCCCACGT CCCAGGAGCC CCTGATGAGA GTGGAGCTGA      2280

AAAAAGAAGC AGGACTGAGG GAGCTGGCCG TGCGACTGGG CTTCGGGCCC TGTGCAGAGG      2340

AGCAGGCCTT CCTGAGCAGG AGGAAGCAGG TGGTGGCCGC GGCCTTGAGG CAGGCCCTGC      2400

AGCTGGATGG AGACCTGCAG GAGGATGAGA TCCCAGTGGT AGCTATTATG CCACTGGTG       2460

GTGGGATCCG GGCAATGACT TCCCTGTATG GGCAGCTGGC TGGCCTGAAG GAGCTGGGCC      2520

TCTTGGATTG CGTCTCCTAC ATCACCGGGG CCTCGGGCTC CACCTGGGCC TTGGCCAACC      2580

TTTATGAGGA CCCAGAGTGG TCTCAGAAGG ACCTGGCAGG GCCCACTGAG TTGCTGAAGA      2640

CCCAGGTGAC CAAGAACAAG CTGGGTGTGC TGGCCCCCAG CCAGCTGCAG CGGTACCGGC      2700

AGGAGCTGGC CGAGCGTGCC CGCTTGGGCT ACCCAAGCTG CTTCACCAAC CTGTGGGCCC      2760

TCATCAACGA GGCGCTGCTG CATGATGAGC CCATGATCA CAAGCTCTCA GATCAACGGG       2820

AGGCCCTGAG TCATGGCCAG AACCCTCTGC CCATCTACTG TGCCCTCAAC ACCAAAGGGC      2880

AGAGCCTGAC CACTTTTGAA TTTGGGGAGT GGTGCGAGTT CTCTCCCTAC GAGGTCGGCT      2940

TCCCCAAGTA CGGGGCCTTC ATCCCCTCTG AGCTCTTTGG CTCCGAGTTC TTTATGGGGC      3000

AGCTGATGAA GAGGCTTCCT GAGTCCCGCA TCTGCTTCTT AGAAGGTATC TGGAGCAACC      3060

TGTATCAGC CAACCTCCAG GACAGCTTAT ACTGGGCCTC AGAGCCCAGC CAGTTCTGGG       3120

ACCGCTGGGT CAGGAACCAG GCCAACCTGG ACAAGGAGCA GGTCCCCCTT CTGAAGATAG      3180

AAGAACCACC CTCAACAGCC GGCAGGATAG CTGAGTTTTT CACCGATCTT CTGACGTGGC      3240

GTCCACTGGC CCAGGCCACA CATAATTTCC TGCGTGGCCT CCATTTCCAC AAAGACTACT      3300

TTCAGCATCC TCACTTCTCC ACATGGAAAG CTACCACTCT GGATGGGCTC CCCAACCAGC      3360

TGACACCCTC GGAGCCCCAC CTGTGCCTGC TGGATGTTGG CTACCTCATC AATACCAGCT      3420

GCCTGCCCCT CCTGCAGCCC ACTCGGGACG TGGACCTCAT CCTGTCATTG GACTACAACC      3480

TCCACGGAGC CTTCCAGCAG TTGCAGCTCC TGGGCCGGTT CTGCCAGGAG CAGGGGATCC      3540

CGTTCCCACC CATCTCGCCC AGCCCCGAAG AGCAGCTCCA GCCTCGGGAG TGCCACACCT      3600

TCTCCGACCC CACCTGCCCC GGAGCCCCTG CGGTGCTGCA CTTTCCTCTG GTCAGCGACT      3660

CCTTCCGGGA GTACTCGGCC CCTGGGGTCC GGCGGACACC CGAGGAGGCG GCAGCTGGGG      3720

AGGTGAACCT GTCTTCATCG GACTCTCCCT ACCACTACAC GAAGGTGACC TACAGCCAGG      3780

AGGACGTGGA CAAGCTGCTG CACCTGACAC ATTACAATGT CTGCAACAAC CAGGAGCAGC      3840

TGCTGGAGGC TCTGCGCCAG GCAGTGCAGC GGAGGCGGCA GCGCAGGCCC CACTGATGGC      3900

CGGGGCCCCT GCCACCCCTA ACTCTCATTC ATTCCCTGGC TGCTGAGTTG CAGGTGGGAA      3960

CTGTCATCAC GCAGTGCTTC AGAGCCTCGG GCTCAGGTGG CACTGTCCCA GGGTCCAGGC      4020

TGAGGGCTGG GAGCTCCCTT GCGCCTCAGC AGTTTGCAGT GGGGTAAGGA GGCCAAGCCC      4080

ATTTGTGTAA TCACCCAAAA CCCCCGGCC TGTGCCTGTT TTCCCTTCTG CGCTACCTTG       4140

AGTAGTTGGA GCACTTGATA CATCACAGAC TCATACAAAT GTG                        4183
```

(2) INFORMATION FOR SEQ ID NO: 2:

(i) SEQUENCE CHARACTERISTICS:
        (A) LENGTH: 778 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 2:

```
Ala Glu Val Ser Arg Thr Cys Leu Leu Thr Val Arg Val Leu Gln Ala
1               5                   10                  15

His Arg Leu Pro Ser Lys Asp Leu Val Thr Pro Ser Asp Cys Tyr Val
            20                  25                  30

Thr Leu Trp Leu Pro Thr Ala Cys Ser His Arg Leu Gln Thr Arg Thr
        35                  40                  45

Val Lys Asn Ser Ser Ser Pro Val Trp Asn Gln Ser Phe His Phe Arg
50                  55                  60

Ile His Arg Gln Leu Lys Asn Val Met Glu Leu Lys Val Phe Asp Gln
65                  70                  75                  80

Asp Leu Val Thr Gly Asp Asp Pro Val Leu Ser Val Leu Phe Asp Ala
                85                  90                  95

Gly Thr Leu Arg Ala Gly Glu Phe Arg Arg Glu Ser Phe Ser Leu Ser
            100                 105                 110

Pro Gln Gly Glu Gly Arg Leu Glu Val Glu Phe Arg Leu Gln Ser Leu
        115                 120                 125

Ala Asp Arg Gly Glu Trp Leu Val Ser Asn Gly Val Leu Val Ala Arg
130                 135                 140

Glu Leu Ser Cys Leu His Val Gln Leu Glu Glu Thr Gly Asp Gln Lys
145                 150                 155                 160

Ser Ser Glu His Arg Val Gln Leu Val Val Pro Gly Ser Cys Glu Gly
                165                 170                 175

Pro Gln Glu Ala Ser Val Gly Thr Gly Thr Phe Arg Phe His Cys Pro
            180                 185                 190

Ala Cys Trp Glu Gln Glu Leu Ser Ile Arg Leu Gln Asp Ala Pro Glu
        195                 200                 205

Glu Gln Leu Lys Ala Pro Leu Ser Ala Leu Pro Ser Gly Gln Val Val
210                 215                 220

Arg Leu Val Phe Pro Thr Ser Gln Glu Pro Leu Met Arg Val Glu Leu
225                 230                 235                 240

Lys Lys Glu Ala Gly Leu Arg Glu Leu Ala Val Arg Leu Gly Phe Gly
                245                 250                 255

Pro Cys Ala Glu Glu Gln Ala Phe Leu Ser Arg Arg Lys Gln Val Val
            260                 265                 270

Ala Ala Ala Leu Arg Gln Ala Leu Gln Leu Asp Gly Asp Leu Gln Glu
        275                 280                 285

Asp Glu Ile Pro Val Val Ala Ile Met Ala Thr Gly Gly Gly Ile Arg
290                 295                 300

Ala Met Thr Ser Leu Tyr Gly Gln Leu Ala Gly Leu Lys Glu Leu Gly
305                 310                 315                 320

Leu Leu Asp Cys Val Ser Tyr Ile Thr Gly Ala Ser Gly Ser Thr Trp
                325                 330                 335

Ala Leu Ala Asn Leu Tyr Glu Asp Pro Glu Trp Ser Gln Lys Asp Leu
            340                 345                 350
```

-continued

```
Ala Gly Pro Thr Glu Leu Leu Lys Thr Gln Val Thr Lys Asn Lys Leu
        355                 360                 365

Gly Val Leu Ala Pro Ser Gln Leu Gln Arg Tyr Arg Gln Glu Leu Ala
370                 375                 380

Glu Arg Ala Arg Leu Gly Tyr Pro Ser Cys Phe Thr Asn Leu Trp Ala
385                 390                 395                 400

Leu Ile Asn Glu Ala Leu Leu His Asp Glu Pro His Asp His Lys Leu
                405                 410                 415

Ser Asp Gln Arg Glu Ala Leu Ser His Gly Gln Asn Pro Leu Pro Ile
            420                 425                 430

Tyr Cys Ala Leu Asn Thr Lys Gly Gln Ser Leu Thr Thr Phe Glu Phe
        435                 440                 445

Gly Glu Trp Cys Glu Phe Ser Pro Tyr Glu Val Gly Phe Pro Lys Tyr
        450                 455                 460

Gly Ala Phe Ile Pro Ser Glu Leu Phe Gly Ser Glu Phe Phe Met Gly
465                 470                 475                 480

Gln Leu Met Lys Arg Leu Pro Glu Ser Arg Ile Cys Phe Leu Glu Gly
                485                 490                 495

Ile Trp Ser Asn Leu Tyr Ala Ala Asn Leu Gln Asp Ser Leu Tyr Trp
            500                 505                 510

Ala Ser Glu Pro Ser Gln Phe Trp Asp Arg Trp Val Arg Asn Gln Ala
        515                 520                 525

Asn Leu Asp Lys Glu Gln Val Pro Leu Leu Lys Ile Glu Glu Pro Pro
        530                 535                 540

Ser Thr Ala Gly Arg Ile Ala Glu Phe Phe Thr Asp Leu Leu Thr Trp
545                 550                 555                 560

Arg Pro Leu Ala Gln Ala Thr His Asn Phe Leu Arg Gly Leu His Phe
                565                 570                 575

His Lys Asp Tyr Phe Gln His Pro His Phe Ser Thr Trp Lys Ala Thr
            580                 585                 590

Thr Leu Asp Gly Leu Pro Asn Gln Leu Thr Pro Ser Glu Pro His Leu
        595                 600                 605

Cys Leu Leu Asp Val Gly Tyr Leu Ile Asn Thr Ser Cys Leu Pro Leu
        610                 615                 620

Leu Gln Pro Thr Arg Asp Val Asp Leu Ile Leu Ser Leu Asp Tyr Asn
625                 630                 635                 640

Leu His Gly Ala Phe Gln Gln Leu Gln Leu Leu Gly Arg Phe Cys Gln
                645                 650                 655

Glu Gln Gly Ile Pro Phe Pro Pro Ile Ser Pro Ser Pro Glu Glu Gln
            660                 665                 670

Leu Gln Pro Arg Glu Cys His Thr Phe Ser Asp Pro Thr Cys Pro Gly
        675                 680                 685

Ala Pro Ala Val Leu His Phe Pro Leu Val Ser Asp Ser Phe Arg Glu
        690                 695                 700

Tyr Ser Ala Pro Gly Val Arg Arg Thr Pro Glu Ala Ala Ala Gly
705                 710                 715                 720

Glu Val Asn Leu Ser Ser Ser Asp Ser Pro Tyr His Tyr Thr Lys Val
                725                 730                 735

Thr Tyr Ser Gln Glu Asp Val Asp Lys Leu Leu His Leu Thr His Tyr
            740                 745                 750
```

```
Asn Val Cys Asn Asn Gln Glu Gln Leu Leu Glu Ala Leu Arg Gln Ala
        755                 760                 765

Val Gln Arg Arg Arg Gln Arg Arg Pro His
        770                 775

(2) INFORMATION FOR SEQ ID NO: 3:

(i) SEQUENCE CHARACTERISTICS:
        (A) LENGTH: 2699 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

TCTAGAGAAT TCACCACCAT GGACTACAAG GACGACGATG ACAAGTCATT TATAGATCCT        60

TACCAGCACA TTATAGCAGA GGTGTCCAGG ACCTGCCTGC TCACGGTTCG TGTCCTGCAG       120

GCCCATCGCC TACCCTCTAA GGACCTAGTG ACCCCCTCTG ACTGCTACGT GACTCTCTGG       180

CTGCCCACGG CCTGCAGCCA CAGGCTCCAG ACACGCACGG TCAAGAACAG CAGTAGCCCT       240

GTCTGGAACC AGAGCTTTCA CTTCAGGATC CACAGGCAGC TCAAGAATGT CATGGAACTG       300

AAAGTCTTTG ACCAGGACCT GGTGACCGGA GATGACCCTG TGTTGTCAGT ACTGTTTGAT       360

GCGGGGACTC TGCGGGCTGG GGAGTTCCGG CGCGAGAGCT TCTCACTGAG CCCTCAGGGT       420

GAGGGGCGCC TGGAAGTTGA ATTTCGCCTG CAGAGTCTGG CTGACCGTGG CGAGTGGCTC       480

GTCAGCAATG GCGTTCTGGT GGCCCGGGAG CTCTCCTGCT GCACGTTCA ACTGGAGGAG        540

ACAGGAGACC AGAAGTCCTC AGAGCACAGA GTTCAGCTTG TGGTTCCTGG GTCCTGTGAG       600

GGTCCGCAGG AGGCCTCTGT GGGCACTGGC ACCTTCCGCT TCCACTGCCC AGCCTGCTGG       660

GAGCAGGAGC TGAGTATTCG CCTGCAGGAT GCCCCCGAGG AGCAACTAAA GGCGCCACTG       720

AGTGCCCTGC CCTCTGGTCA AGTGGTGAGG CTTGTCTTCC CCACGTCCCA GGAGCCCCTG       780

ATGAGAGTGG AGCTGAAAAA AGAAGCAGGA CTGAGGGAGC TGGCCGTGCG ACTGGGCTTC       840

GGGCCCTGTG CAGAGGAGCA GGCCTTCCTG AGCAGGAGGA AGCAGGTGGT GGCCGCGGCC       900

TTGAGGCAGG CCCTGCAGCT GGATGGAGAC CTGCAGGAGG ATGAGATCCC AGTGGTAGCT       960

ATTATGGCCA CTGGTGGTGG GATCCGGGCA ATGACTTCCC TGTATGGGCA GCTGGCTGGC      1020

CTGAAGGAGC TGGGCCTCTT GGATTGCGTC TCCTACATCA CCGGGGCCTC GGGCTCCACC      1080

TGGGCCTTGG CCAACCTTTA TGAGGACCCA GAGTGGTCTC AGAAGGACCT GGCAGGGCCC      1140

ACTGAGTTGC TGAAGACCCA GGTGACCAAG AACAAGCTGG GTGTGCTGGC CCCCAGCCAG      1200

CTGCAGCGGT ACCGGCAGGA GCTGGCCGAG CGTGCCCGCT GGGCTACCC AAGCTGCTTC       1260

ACCAACCTGT GGGCCCTCAT CAACGAGGCG CTGCTGCATG ATGAGCCCCA TGATCACAAG      1320

CTCTCAGATC AACGGGAGGC CCTGAGTCAT GGCCAGAACC CTCTGCCCAT CTACTGTGCC      1380

CTCAACACCA AGGGCAGAG CCTGACCACT TTTGAATTTG GGGAGTGGTG CGAGTTCTCT       1440

CCCTACGAGG TCGGCTTCCC CAAGTACGGG GCCTTCATCC CCTCTGAGCT CTTTGGCTCC      1500

GAGTTCTTTA TGGGGCAGCT GATGAAGAGG CTTCCTGAGT CCCGCATCTG CTTCTTAGAA      1560

GGTATCTGGA GCAACCTGTA TGCAGCCAAC CTCCAGGACA GCTTATACTG GGCCTCAGAG      1620

CCCAGCCAGT TCTGGGACCG CTGGGTCAGG AACCAGGCCA ACCTGGACAA GGAGCAGGTC      1680

CCCCTTCTGA AGATAGAAGA ACCACCCTCA CAGCCGGCA GGATAGCTGA GTTTTTCACC       1740

GATCTTCTGA CGTGGCGTCC ACTGGCCCAG GCCACACATA ATTTCCTGCG TGGCCTCCAT      1800
```

-continued

```
TTCCACAAAG ACTACTTTCA GCATCCTCAC TTCTCCACAT GGAAAGCTAC CACTCTGGAT    1860

GGGCTCCCCA ACCAGCTGAC ACCCTCGGAG CCCCACCTGT GCCTGCTGGA TGTTGGCTAC    1920

CTCATCAATA CCAGCTGCCT GCCCCTCCTG CAGCCCACTC GGGACGTGGA CCTCATCCTG    1980

TCATTGGACT ACAACCTCCA CGGAGCCTTC AGCAGTTGC AGCTCCTGGG CCGGTTCTGC    2040

CAGGAGCAGG GGATCCCGTT CCCACCCATC TCGCCCAGCC CCGAAGAGCA GCTCCAGCCT    2100

CGGGAGTGCC ACACCTTCTC CGACCCCACC TGCCCCGGAG CCCCTGCGGT GCTGCACTTT    2160

CCTCTGGTCA GCGACTCCTT CCGGGAGTAC TCGGCCCCTG GGGTCCGGCG GACACCCGAG    2220

GAGGCGGCAG CTGGGGAGGT GAACCTGTCT TCATCGGACT CTCCCTACCA CTACACGAAG    2280

GTGACCTACA GCCAGGAGGA CGTGGACAAG CTGCTGCACC TGACACATTA CAATGTCTGC    2340

AACAACCAGG AGCAGCTGCT GGAGGCTCTG CGCCAGGCAG TGCAGCGGAG GCGGCAGCGC    2400

AGGCCCCACT GATGGCCGGG GCCCCTGCCA CCCCTAACTC TCATTCATTC CCTGGCTGCT    2460

GAGTTGCAGG TGGAACTGT CATCACGCAG TGCTTCAGAG CCTCGGGCTC AGGTGGCACT    2520

GTCCCAGGGT CCAGGCTGAG GGCTGGGAGC TCCCTTGCGC CTCAGCAGTT TGCAGTGGGG    2580

TAAGGAGGCC AAGCCCATTT GTGTAATCAC CCAAAACCCC CCGGCCTGTG CCTGTTTTCC    2640

CTTCTGCGCT ACCTTGAGTA GTTGGAGCAC TTGATACATC ACAGACTCAT ACAAATGTG     2699
```

(2) INFORMATION FOR SEQ ID NO: 4:

(i) SEQUENCE CHARACTERISTICS:
        (A) LENGTH: 797 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 4:

```
Met Asp Tyr Lys Asp Asp Asp Lys Ser Phe Ile Asp Pro Tyr Gln
1               5                   10                  15

His Ile Ile Ala Glu Val Ser Arg Thr Cys Leu Leu Thr Val Arg Val
            20                  25                  30

Leu Gln Ala His Arg Leu Pro Ser Lys Asp Leu Val Thr Pro Ser Asp
        35                  40                  45

Cys Tyr Val Thr Leu Trp Leu Pro Thr Ala Cys Ser His Arg Leu Gln
50                  55                  60

Thr Arg Thr Val Lys Asn Ser Ser Pro Val Trp Asn Gln Ser Phe
65                  70                  75                  80

His Phe Arg Ile His Arg Gln Leu Lys Asn Val Met Glu Leu Lys Val
                85                  90                  95

Phe Asp Gln Asp Leu Val Thr Gly Asp Pro Val Leu Ser Val Leu
            100                 105                 110

Phe Asp Ala Gly Thr Leu Arg Ala Gly Glu Phe Arg Arg Glu Ser Phe
        115                 120                 125

Ser Leu Ser Pro Gln Gly Glu Gly Arg Leu Glu Val Glu Phe Arg Leu
130                 135                 140

Gln Ser Leu Ala Asp Arg Gly Glu Trp Leu Val Ser Asn Gly Val Leu
145                 150                 155                 160

Val Ala Arg Glu Leu Ser Cys Leu His Val Gln Leu Glu Glu Thr Gly
                165                 170                 175

Asp Gln Lys Ser Ser Glu His Arg Val Gln Leu Val Val Pro Gly Ser
            180                 185                 190
```

-continued

```
Cys Glu Gly Pro Gln Glu Ala Ser Val Gly Thr Gly Thr Phe Arg Phe
        195                 200                 205

His Cys Pro Ala Cys Trp Glu Gln Glu Leu Ser Ile Arg Leu Gln Asp
    210                 215                 220

Ala Pro Glu Glu Gln Leu Lys Ala Pro Leu Ser Ala Leu Pro Ser Gly
225                 230                 235                 240

Gln Val Val Arg Leu Val Phe Pro Thr Ser Gln Glu Pro Leu Met Arg
                245                 250                 255

Val Glu Leu Lys Lys Glu Ala Gly Leu Arg Glu Leu Ala Val Arg Leu
            260                 265                 270

Gly Phe Gly Pro Cys Ala Glu Gln Ala Phe Leu Ser Arg Arg Lys
        275                 280                 285

Gln Val Val Ala Ala Leu Arg Gln Ala Leu Gln Leu Asp Gly Asp
    290                 295                 300

Leu Gln Glu Asp Glu Ile Pro Val Val Ala Ile Met Ala Thr Gly Gly
305                 310                 315                 320

Gly Ile Arg Ala Met Thr Ser Leu Tyr Gly Gln Leu Ala Gly Leu Lys
                325                 330                 335

Glu Leu Gly Leu Leu Asp Cys Val Ser Tyr Ile Thr Gly Ala Ser Gly
            340                 345                 350

Ser Thr Trp Ala Leu Ala Asn Leu Tyr Glu Asp Pro Glu Trp Ser Gln
        355                 360                 365

Lys Asp Leu Ala Gly Pro Thr Glu Leu Leu Lys Thr Gln Val Thr Lys
    370                 375                 380

Asn Lys Leu Gly Val Leu Ala Pro Ser Gln Leu Gln Arg Tyr Arg Gln
385                 390                 395                 400

Glu Leu Ala Glu Arg Ala Arg Leu Gly Tyr Pro Ser Cys Phe Thr Asn
                405                 410                 415

Leu Trp Ala Leu Ile Asn Glu Ala Leu Leu His Asp Glu Pro His Asp
            420                 425                 430

His Lys Leu Ser Asp Gln Arg Glu Ala Leu Ser His Gly Gln Asn Pro
        435                 440                 445

Leu Pro Ile Tyr Cys Ala Leu Asn Thr Lys Gly Gln Ser Leu Thr Thr
    450                 455                 460

Phe Glu Phe Gly Glu Trp Cys Glu Phe Ser Pro Tyr Glu Val Gly Phe
465                 470                 475                 480

Pro Lys Tyr Gly Ala Phe Ile Pro Ser Glu Leu Phe Gly Ser Glu Phe
                485                 490                 495

Phe Met Gly Gln Leu Met Lys Arg Leu Pro Glu Ser Arg Ile Cys Phe
            500                 505                 510

Leu Glu Gly Ile Trp Ser Asn Leu Tyr Ala Ala Asn Leu Gln Asp Ser
        515                 520                 525

Leu Tyr Trp Ala Ser Glu Pro Ser Gln Phe Trp Asp Arg Trp Val Arg
    530                 535                 540

Asn Gln Ala Asn Leu Asp Lys Glu Gln Val Pro Leu Leu Lys Ile Glu
545                 550                 555                 560

Glu Pro Pro Ser Thr Ala Gly Arg Ile Ala Glu Phe Phe Thr Asp Leu
                565                 570                 575

Leu Thr Trp Arg Pro Leu Ala Gln Ala Thr His Asn Phe Leu Arg Gly
            580                 585                 590

Leu His Phe His Lys Asp Tyr Phe Gln His Pro His Phe Ser Thr Trp
        595                 600                 605
```

```
Lys Ala Thr Thr Leu Asp Gly Leu Pro Asn Gln Leu Thr Pro Ser Glu
610                 615                 620

Pro His Leu Cys Leu Leu Asp Val Gly Tyr Leu Ile Asn Thr Ser Cys
625                 630                 635                 640

Leu Pro Leu Leu Gln Pro Thr Arg Asp Val Asp Leu Ile Leu Ser Leu
                645                 650                 655

Asp Tyr Asn Leu His Gly Ala Phe Gln Gln Leu Gln Leu Leu Gly Arg
                660                 665                 670

Phe Cys Gln Glu Gln Gly Ile Pro Phe Pro Pro Ile Ser Pro Ser Pro
            675                 680                 685

Glu Glu Gln Leu Gln Pro Arg Glu Cys His Thr Phe Ser Asp Pro Thr
690                 695                 700

Cys Pro Gly Ala Pro Ala Val Leu His Phe Pro Leu Val Ser Asp Ser
705                 710                 715                 720

Phe Arg Glu Tyr Ser Ala Pro Gly Val Arg Arg Thr Pro Glu Glu Ala
                725                 730                 735

Ala Ala Gly Glu Val Asn Leu Ser Ser Ser Asp Ser Pro Tyr His Tyr
            740                 745                 750

Thr Lys Val Thr Tyr Ser Gln Glu Asp Val Asp Lys Leu Leu His Leu
            755                 760                 765

Thr His Tyr Asn Val Cys Asn Asn Gln Glu Gln Leu Leu Glu Ala Leu
770                 775                 780

Arg Gln Ala Val Gln Arg Arg Gln Arg Arg Pro His
785                 790                 795

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 5:

CCTCCTGCAG CCCACTCGGG AC                                          22

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 6:

GCTGACCAGA GGAAAGTGCA GC                                          22

(2) INFORMATION FOR SEQ ID NO: 7:

(i) SEQUENCE CHARACTERISTICS:
        (A) LENGTH: 144 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"
```

-continued (xi) SEQUENCE DESCRIPTION: SEQ ID NO: 7:

```
CTAGAGAATT CACCACCATG GACTACAAGG ACGACGATGA CAAGTCATTT ATAGATCCTT      60

ACCAGCACAT TATAGCAGAG GTGTCCAGGA CCTGCCTGCT CACGGTTCGT GTCCTGCAGG     120

CCCATCGCCT ACCCTCTAAG GACC                                           144
```

(2) INFORMATION FOR SEQ ID NO: 8:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 8:

```
TCTTAAGTGG TGGTACCTGA TGTTCCTGCT GCTACTGTTC AGTAAATATC TAGGAATGGT      60

CGTGTAATAT CGTCTCCACA GGTCCTGGAC GGACGAGTGC CAAGCACAGG ACGTCCGGGT     120

AGCGGATGGG AGATTCCTGG AT                                             142
```

(2) INFORMATION FOR SEQ ID NO: 9:

(i) SEQUENCE CHARACTERISTICS:
        (A) LENGTH: 35 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

```
Met Asp Tyr Lys Asp Asp Asp Lys Ser Phe Ile Asp Pro Tyr Gln
1               5                   10                  15

His Ile Ile Ala Glu Val Ser Arg Thr Cys Leu Leu Thr Val Arg Val
                20                  25                  30

Leu Gln Ala
        35
```

CYTOSOLIC PHOSPHOLIPASE A$_2$-BETA ENZYMES

The present application is a divisional of U.S. application Ser. No. 09/895,547, filed Jun. 29, 2001, now is U.S. Pat. No. 6,468,625 which is a divisional of U.S. application Ser. No. 09/460,145, filed Dec. 13, 1999, now U.S. Pat. No. 6,287,838, which is a continuation of U.S. application Ser. No. 08/788,975, filed Jan. 24, 1997, now abandoned. The contents of U.S. application Ser. No. 08/788,975, including any drawing figures and/or sequence listings, are being relied upon and are incorporated herein by reference.

The present invention relates to a purified cytosolic phospholipase A$_2$-Beta (cPLA$_2$-β) enzymes which are useful for assaying chemical agents for anti-inflammatory activity.

BACKGROUND OF THE INVENTION

The phospholipase A$_2$ enzymes comprise a widely distributed family of enzymes which catalyze the hydrolysis of the acyl ester bond of glycerophospholipids at the sn-2 position. One kind of phospholipase A$_2$ enzymes, secreted phospholipase A$_2$ or sPLA$_2$, are involved in a number of biological functions, including phospholipid digestion, the toxic activities of numerous venoms, and potential antibacterial activities. A second kind of phospholipase A$_2$ enzymes, the intracellular phospholipase A$_2$ enzymes, also known as cytosolic phospholipase A$_2$ or cPLA$_2$, are active in membrane phospholipid turnover and in regulation of intracellular signalling mediated by the multiple components of the well-known arachidonic acid cascade. One or more cPLA$_2$ enzymes are believed to be responsible for the rate limiting step in the arachidonic acid cascade, namely, release of arachidonic acid from membrane glycerophospholipids. The action of cPLA$_2$ also results in biosynthesis of platelet activating factor (PAF). U.S. Pat. Nos. 5,322,776, 5,354,677, 5,527,698 and 5,593,878 disclose such enzymes (sometimes referred to herein as "cPLA$_2$α").

The phospholipase B enzymes are a family of enzymes which catalyze the hydrolysis of the acyl ester bond of glycerophospholipids at the sn-1 and sn-2 positions. The mechanism of hydrolysis is unclear but may consist of initial hydrolysis of the sn-2 fatty acid followed by rapid cleavage of the sn-1 substituent, i.e., functionally equivalent to the combination of phospholipase A$_2$ and lysophospholipase (Saito et al., Methods of Enzymol., 1991, 197, 446; Gassama-Diagne et al., J. Biol. Chem., 1989, 264, 9470). Whether these two events occur at the same or two distinct active sites has not been resolved. It is also unknown if these enzymes have a preference for the removal of unsaturated fatty acids, in particular arachidonic acid, at the sn-2 position and accordingly contribute to the arachidonic acid cascade.

Upon release from the membrane, arachidonic acid may be metabolized via the cyclooxygenase pathway to produce the various prostaglandins and thromboxanes, or via the lipoxygenase pathway to produce the various leukotrienes and related compounds. The prostaglandins, leukotrienes and platelet activating factor are well known mediators of various inflammatory states, and numerous anti-inflammatory drugs have been developed which function by inhibiting one or more steps in the arachidonic acid cascade. The efficacy of the present anti-inflammatory drugs which act through inhibition of arachidonic acid cascade steps is limited by the existence of side effects which may be harmful to various individuals.

A very large industrial effort has been made to identify additional anti-inflammatory drugs which inhibit the arachidonic acid cascade. In general, this industrial effort has employed the secreted phospholipase A$_2$ enzymes in inhibitor screening assays, for example, as disclosed in U.S. Pat. No. 4,917,826. However, because the secreted phospholipase A$_2$ enzymes are extracellular proteins (i.e., not cytosolic) and do not selectively hydrolyze arachidonic acid, they are presently not believed to contribute to prostaglandin and leukotriene production. While some inhibitors of the small secreted phospholipase A$_2$ enzymes have been reported to display anti-inflammatory activity, such as bromphenacyl bromide, mepacrine, and certain butyrophenones as disclosed in U.S. Pat. No. 4,239,780. The site of action of these compounds is unclear as these agents retain anti-inflammatory activity in mouse strains lacking sPLA$_2$. It is presently believed that inhibitor screening assays should employ cytosolic phospholipase A$_2$ enzymes which initiate the arachidonic acid cascade.

An improvement in the search for anti-inflammatory drugs which inhibit the arachidonic acid cascade was developed in commonly assigned U.S. Pat. No. 5,322,776, incorporated herein by reference. In that application, a cytosolic form of phospholipase A$_2$ was identified, isolated, and cloned. Use of the cytosolic form of phospholipase A$_2$ to screen for anti-inflammatory drugs provides a significant improvement in identifying inhibitors of the arachidonic acid cascade. The cytosolic phospholipase A$_2$ disclosed in U.S. Pat. No. 5,322,776 is a 110 kD protein which depends on the presence of elevated levels of calcium inside the cell for its activity. The cPLA$_2$ of U.S. Pat. No. 5,322,776 plays a pivotal role in the production of leukotrienes and prostaglandins initiated by the action of pro-inflammatory cytokines and calcium mobilizing agents. The cPLA$_2$ of U.S. Pat. No. 5,322,776 is activated by phosphorylation on serine residues and increasing levels of intracellular calcium, resulting in translocation of the enzyme from the cytosol to the membrane where arachidonic acid is selectively hydrolyzed from membrane phospholipids.

In addition to the cPLA$_2$ of U.S. Pat. No. 5,322,776, some cells contain calcium independent phospholipase A$_2$/B enzymes. For example, such enzymes have been identified in rat, rabbit, canine and human heart tissue (Gross, TCM, 1991, 2, 115; Zupan et al., J. Med. Chem., 1993, 36, 95; Hazen et al., J. Clin. Invest., 1993, 91, 2513; Lehman et al., J. Biol. Chem., 1993, 268, 20713; Zupan et al., J. Biol. Chem., 1992, 267, 8707; Hazen et al., J. Biol. Chem., 1991, 266, 14526; Loeb et al., J. Biol. Chem., 1986, 261, 10467; Wolf et al., J. Biol. Chem., 1985, 260, 7295; Hazen et al., Meth. Enzymol., 1991, 197, 400; Hazen et al., J. Biol. Chem., 1990, 265, 10622; Hazen et al., J. Biol. Chem., 1993, 268, 9892; Ford et al., J. Clin. Invest., 1991, 88, 331; Hazen et al., J. Biol. Chem., 1991, 266, 5629; Hazen et al., Circulation Res., 1992, 70, 486; Hazen et al., J. Biol. Chem., 1991, 266, 7227; Zupan et al., FEBS, 1991, 284, 27), as well as rat and human pancreatic islet cells (Ramanadham et al., Biochemistry, 1993, 32, 337; Gross et al., Biochemistry, 1993, 32, 327), in the macrophage-like cell line, P388D$_1$ (Ulevitch et al., J. Biol. Chem., 1988, 263, 3079; Ackermann et al., J. Biol. Chem., 1994, 269, 9227; Ross et al., Arch. Biochem. Biophys., 1985, 238, 247; Ackermann et al., FASEB Journal, 1993, 7(7), 1237), in various rat tissue cytosols (Nijssen et al., Biochim. Biophys. Acta, 1986, 876, 611; Pierik et al., Biochim. Biophys. Acta, 1988, 962, 345; Aarsman et al., J. Biol. Chem., 1989, 264, 10008), bovine brain (Ueda et al., Biochem. Biophys, Res. Comm., 1993, 195, 1272; Hirashima et al., J. Neurochem., 1992, 59, 708), in yeast (*Saccharomyces cerevisiae*) mitochondria (Yost et al., Biochem. International, 1991, 24, 199), hamster heart cytosol (Cao et al., J. Biol. Chem., 1987, 262, 16027), rabbit lung microsomes (Angle et al., Biochim. Biophys. Acta, 1988, 962, 234) and guinea pig intestinal brush-border membrane (Gassama-Diagne et al., J. Biol. Chem., 1989, 264, 9470). U.S. Pat. Nos. 5,466,595, 5,554,511 and 5,589, 170 also disclose calcium independent $cPLA_2/B$ enzymes (sometimes referred to herein as "$iPLA_2$").

It is believed that the phospholipase enzymes may perform important functions in release of arachidonic acid in specific tissues which are characterized by unique membrane phospholipids, by generating lysophospholipid species which are deleterious to membrane integrity or by remodeling of unsaturated species of membrane phospholipids through deacylation/reacylation mechanisms. The activity of such a phospholipase may well be regulated by mechanisms that are different from that of the $cPLA_2$ of U.S. Pat. No. 5,322,776. In addition the activity may be more predominant in certain inflamed tissues over others.

Therefore, it would be desirable to identify and isolate additional $cPLA_2$ enzymes.

SUMMARY OF THE INVENTION

In other embodiments, the invention provides isolated polynucleotides comprising a nucleotide sequence selected from the group consisting of:

(a) the nucleotide sequence of SEQ ID NO:1;

(b) a nucleotide sequence encoding the amino acid sequence of SEQ ID NO:2;

(c) a nucleotide sequence encoding a fragment of the amino acid sequence of SEQ ID NO:2 having activity in a mixed micelle assay with 1-palmitoyl-2-[$^{14}C$]-arachidonyl-phosphatidylcholine;

(d) a nucleotide sequence capable of hybridizing with the sequence of (a), (b) or (c) which encodes a peptide having activity in a mixed micelle assay with 1-palmitoyl-2-[$^{14}C$]-arachidonyl-phosphatidylcholin;

(e) allelic variants of the sequence of (a);

(f) the nucleotide sequence of SEQ ID NO:3;

(g) a nucleotide sequence encoding the amino acid sequence of SEQ ID NO:4;

(h) a nucleotide sequence encoding a fragment of the amino acid sequence of SEQ ID NO:4 having activity in a mixed micelle assay with 1-palmitoyl-2-[$^{14}C$]-arachidonyl-phosphatidylcholine; and (i) a nucleotide sequence capable of hybridizing with the sequence of (f), (g) or (h) which encodes a peptide having activity in a mixed micelle assay with 1-palmitoyl-2-[$^{14}C$]-arachidonyl-phosphatidylcholin.

Expression vectors comprising such polynucleotides and host cells transformed with such vectors are also provided by the present invention. Compositions comprising peptides encoded by such polynucleotides are also provided.

The present invention also provides processes for producing a phospholipase enzyme, said process comprising: (a) establishing a culture of the host cell transformed with a $cPLA_2$-Beta encoding polynucleotide in a suitable culture medium; and (b) isolating said enzyme from said culture. Compositions comprising a peptide made according to such processes are also provided.

Certain embodiments of the present invention provide compositions comprising a peptide comprising an amino acid sequence selected from the group consisting of:

(a) the amino acid sequence of SEQ ID NO:2;

(b) a fragment of the amino acid sequence of SEQ ID NO:2 having activity in a mixed micelle assay with 1-palmitoyl-2-[$^{14}C$]-arachidonyl-phosphatidylcholine;

(c) the amino acid sequence of SEQ ID NO:4; and (d) a fragment of the amino acid sequence of SEQ ID NO:4 having activity in a mixed micelle assay with 1-palmitoyl-2-[$^{14}C$]-arachidonyl-phosphatidylcholine.

The present invention also provides methods for identifying an inhibitor of phospholipase activity, said method comprising: (a) combining a phospholipid, a candidate inhibitor compound, and a composition comprising a phospholipase enzyme peptide; and (b) observing whether said phospholipase enzyme peptide cleaves said phospholipid and releases fatty acid thereby, wherein the peptide composition is one of those described above. Inhibitor of phospholipase activity identified by such methods, pharmaceutical compositions comprising a therapeutically effective amount of such inhibitors and a pharmaceutically acceptable carrier, and methods of reducing inflammation by administering such pharmaceutical compositions to a mammalian subject are also provided.

Polyclonal and monoclonal antibodies to the peptides of the invention are also provided.

DETAILED DESCRIPTION OF THE INVENTION

Figure 1A:
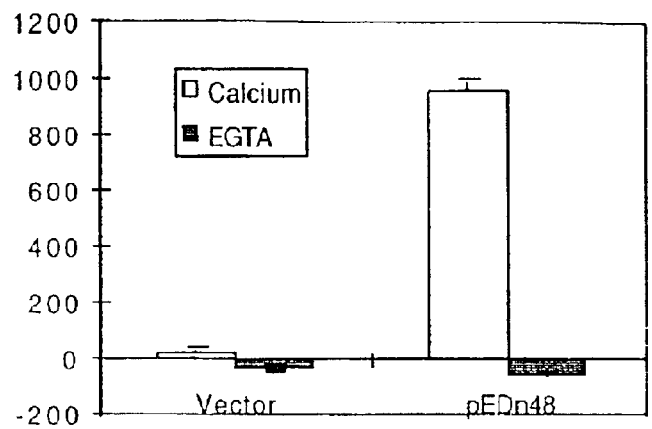
FIG. 1A presents data evidenceing increased $PLA_2$ activity in cells transfected with pEDΔC-n48.
Figure 1B:
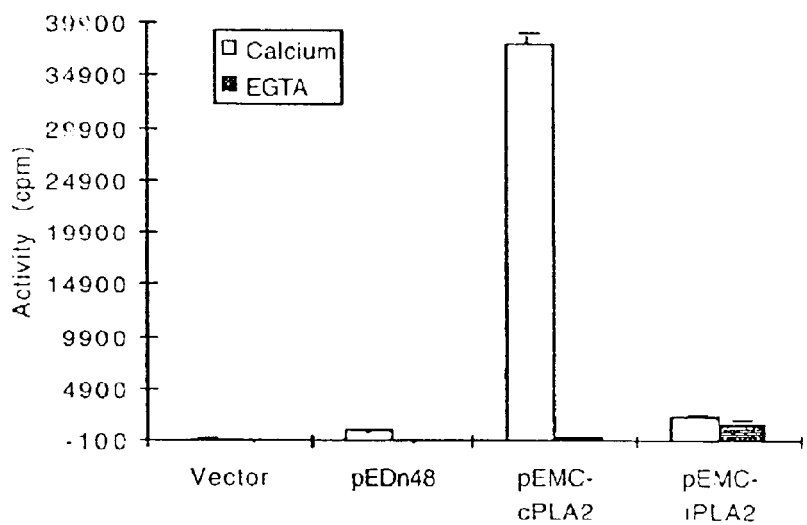
FIG. 1B presents data comparing $PLA_2$ activities of cells transfected with plasmids expressing $cPLA_2\alpha$, $cPLA_2\beta$ and $iPLA_2$.
Figure 2:
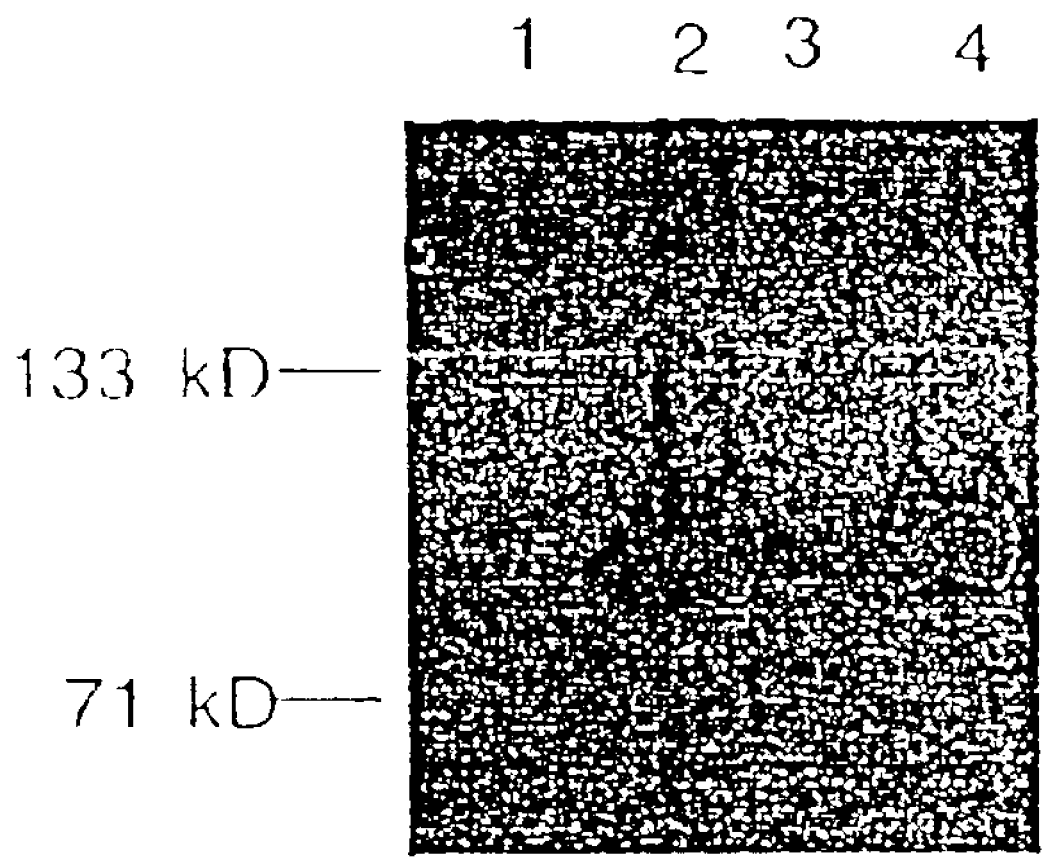
FIG. 2 depicts a gel evidencing the expression of $cPLA_2\beta$ in COS cells.

A cDNA encoding the $cPLA_2$-Beta of the present invention was isolated as described in Example 1. The sequence of the partial cDNA first isolated is reported as SEQ ID NO:1. The amino acid sequence encoded by such cDNA is SEQ ID NO:2. For purposes of expression, as explained in Example 1, polynucleotides encoding N-terminal sequence from $cPLA_2$ was added to the partial cDNA. The polynucleotide sequence of this fusion is reported as SEQ ID NO:3. The amino acid sequence encoded by the fuion cDNA is reported as SEQ ID NO:4.

The invention also encompasses allelic variations of the cDNA sequence as set forth in SEQ ID NO:1 and SEQ ID NO:3, that is, naturally-occurring alternative forms of the cDNAs of SEQ ID NO:1 and SEQ ID NO:3 which also encode phospholipase enzymes of the present invention. Also included in the invention are isolated DNAs which hybridize to the DNA sequence set forth in SEQ ID NO:1 or SEQ ID NO:3 under stringent (e.g. 4×SSC at 65° C. or 50% formamide and 4×SSC at 42° C.), or relaxed (4×SSC at 50° C. or 30–40% formamide at 42° C.) conditions.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the phospholipase enzyme peptides recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the phospholipase enzyme peptide is expressed by a host cell which has been transformed (transfected) with the ligated polynucleotide/expression control sequence.

A number of types of cells may act as suitable host cells for expression of the phospholipase enzyme peptide. Suitable host cells are capable of attaching carbohydrate side chains characteristic of functional phospholipase enzyme peptide. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The phospholipase enzyme peptide may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the phospholipase enzyme peptide in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the phospholipase enzyme peptide is made in yeast or bacteria, it is necessary to attach the appropriate carbohydrates to the appropriate sites on the protein moiety covalently, in order to obtain the glycosylated phospholipase enzyme peptide. Such covalent attachments may be accomplished using known chemical or enzymatic methods.

The phospholipase enzyme peptide of the invention may also be expressed as a product of transgenic animals, e.g., as a component of the milk of transgenic cows, goats, pigs, or sheep which are characterized by somatic or germ cells containing a polynucleotide encoding the phospholipase enzyme peptide.

The phospholipase enzyme peptide of the invention may be prepared by culturing transformed host cells under culture conditions necessary to express a phospholipase enzyme peptide of the present invention. The resulting expressed protein may then be purified from culture medium or cell extracts as described in the examples below.

Alternatively, the phospholipase enzyme peptide of the invention is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the phospholipase enzyme peptide from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media. e.g., silica gel having pendant methyl or other aliphatic groups, can be employed to further purify the phospholipase enzyme peptide. Some or all of the foregoing purification steps, in various combinations, can also be employed to provide a substantially homogeneous isolated recombinant protein. The phospholipase enzyme peptide thus purified is substantially free of other mammalian proteins and is defined in accordance with the present invention as "isolated phospholipase enzyme peptide".

The cPLA$_2$-Beta of the present invention may be used to screen for compounds having anti-inflammatory activity mediated by the various components of the arachidonic acid cascade. Many assays for phospholipase activity are known and may be used with the phospholipase A$_2$-Beta on the present invention to screen unknown compounds. For example, such an assay may be a mixed micelle assay as described in Example 2. Other known phospholipase activity assays include, without limitation, those disclosed in U.S. Pat. No. 5,322,776. These assays may be performed manually or may be automated or robotized for faster screening. Methods of automation and robotization are known to those skilled in the art.

In one possible screening assay, a first mixture is formed by combining a phospholipase enzyme peptide of the present invention with a phospholipid cleavable by such peptide, and the amount of hydrolysis in the first mixture ($B_o$) is measured. A second mixture is also formed by combining the peptide, the phospholipid and the compound or agent to be screened, and the amount of hydrolysis in the second mixture (B) is measured. The amounts of hydrolysis in the first and second mixtures are compared, for example, by performing a $B/B_o$ calculation. A compound or agent is considered to be capable of inhibiting phospholipase activity (i.e., providing anti-inflammatory activity) if a decrease in hydrolysis in the second mixture as compared to the first mixture is observed. The formulation and optimization of mixtures is within the level of skill in the art, such mixtures may also contain buffers and salts necessary to enhance or to optimize the assay, and additional control assays may be included in the screening assay of the invention.

Other uses for the cPLA$_2$-Beta of the present invention are in the development of monoclonal and polyclonal antibodies. Such antibodies may be generated by employing purified forms of the cPLA$_2$ or immunogenic fragments thereof as an antigen using standard methods for the development of polyclonal and monoclonal antibodies as are known to those skilled in the art. Such polyclonal or monoclonal antibodies are useful as research or diagnostic tools, and further may be used to study phospholipase $A_2$ activity and inflammatory conditions.

Pharmaceutical compositions containing anti-inflammatory agents (i.e., inhibitors) identified by the screening method of the present invention may be employed to treat, for example, a number of inflammatory conditions such as rheumatoid arthritis, psoriasis, asthma, inflammatory bowel disease and other diseases mediated by increased levels of prostaglandins, leukotriene, or platelet activating factor. Pharmaceutical compositions of the invention comprise a therapeutically effective amount of a $cPLA_2$ inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 $\mu$g to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

Administration is preferably intravenous, but other known methods of administration for anti-inflammatory agents may be used. Administration of the anti-inflammatory compounds identified by the method of the invention can be carried out in a variety of conventional ways. For example, for topical administration, the anti-inflammatory compound of the invention will be in the form of a pyrogen-free, dermatologically acceptable liquid or semi-solid formulation such as an ointment, cream, lotion, foam or gel. The preparation of such topically applied formulations is within the skill in the art. Gel formulation should contain, in addition to the anti-inflammatory compound, about 2 to about 5% W/W of a gelling agent. The gelling agent may also function to stabilize the active ingredient and preferably should be water soluble. The formulation should also contain about 2% W/V of a bactericidal agent and a buffering agent. Exemplary gels include ethyl, methyl, and propyl celluloses. Preferred gels include carboxypolymethylene such as Carbopol (934P; B.F. Goodrich), hydroxypropyl methylcellulose phthalates such as Methocel (K100M premium; Merril Dow), cellulose gums such as Blanose (7HF; Aqualon, U.K.), xanthan gums such as Keltrol (TF; Kelko International), hydroxyethyl cellulose oxides such as Polyox (WSR 303; Union Carbide), propylene glycols, polyethylene glycols and mixtures thereof. If Carbopol is used, a neutralizing agent, such as NaOH, is also required in order to maintain pH in the desired range of about 7 to about 8 and most desirably at about 7.5. Exemplary preferred bactericidal agents include steryl alcohols, especially benzyl alcohol. The buffering agent can be any of those already known in the art as useful in preparing medicinal formulations, for example 20 mM phosphate buffer, pH 7.5.

Cutaneous or subcutaneous injection may also be employed and in that case the anti-inflammatory compound of the invention will be in the form of pyrogen-free, parenterally acceptable aqueous solutions. The preparation of such parenterally acceptable solutions, having due regard to pH, isotonicity, stability, and the like, is within the skill in the art.

Intravenous injection may be employed, wherein the anti-inflammatory compound of the invention will be in the form of pyrogen-free, parenterally acceptable aqueous solutions A preferred pharmaceutical composition for intravenous injection should contain, in addition to the anti-inflammatory compound, an isotonic vehicle such as Sodium Chloride Injection. Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additive known to those of skill in the art.

The amount of anti-inflammatory compound in the pharmaceutical composition of the present invention will depend upon the nature and severity of the condition being treated, and on the nature of prior treatments which the patient has undergone. Ultimately, the attending physician will decide the amount of anti-inflammatory compound with which to treat each individual patient.

Anti-inflammatory compounds identified using the method of the present invention may be administered alone or in combination with other anti-inflammation agents and therapies.

EXAMPLE 1

Library Construction

Oligo-dT primed and random primed cDNA libraries were constructed from U937 cells using a Poly ATrack kit for isolation of mRNA (Promega), a Superscript Choice kit for the generation of double stranded cDNA (Gibco BRL), and a Lambda ZapII phage cloning kit (Stratagene).

Clone Identification

Two $cPLA_2$-$\beta$ specific deoxyribonucleotides were designed based on the sequence of EST clone W92213:

```
5'-CCTCCTGCAGCCCACTCGGGAC-3'     (SEQ ID NO:5)

5'-GCTGACCAGAGGAAAGTGCAGC-3'     (SEQ ID NO:6)
```

These oligonucleotides were used to screen $10^6$ recombinates of both the oligo dT primed and random primed library. One clone which hybridizes with both oligonucleotides, clone 52A, was examined for complete DNA sequence determination (SEQ ID NO:1). The partial coding sequence on this clone begins at nucleotide 1560 and continues to a stop codon at nucleotide 3894, representing 778 amino acids (see SEQ ID NO:2). The region on the DNA sequence 5' to nucleotide 1560 fits a splice acceptor consensus sequence and is therefore assumed to be unspliced intron sequence.

A comparison of the previous cPLA$_2$ amino acid sequence with the predicted cPLA-β sequence reveals 30% overall identity. It also predicts this clone to be lacking only 11 amino acids from the N-terminus. For this reason we decided to make a chimeric construct using the first 11 amino acids of cPLA$_2$ fused to the 778 amino acids of cPLA$_2$-β. This construct can be used to confirm the activity of the cPLA$_2$-β protein.

Construction of Expression Vectors to Produce cPLA$_2$β Protein in COS-7 Cells:

An adapter was generated using synthesized oligonucleotides. Its sequence and encoded amino acids are shown below.

```
    CTAGAGAATTCACCACCATGGACTACAAGGACGACGATGACAAGTCATTTATAGATCCTT         (SEQ ID NO:7)

1   ---------+---------+---------+---------+---------+---------+    60

TCTTAAGTGGTGGTACCTGATGTTCCTGCTGCTACTGTTCAGTAAATATCTAGGAA         (SEQ ID NO:8)

M   D   Y   K   D   D   D   D   K   S   F   I   D   P   Y -   (SEQ ID NO:9)

Flag-Tag                      cPLA2  linker
    ACCAGCACATTATAGCAGAGGTGTCCAGGACCTGCCTGCTCACGGTTCGTGTCCTGCAGG

61  ---------+---------+---------+---------+---------+---------+    120

TGGTCGTGTAATATCGTCTCCACAGGTCCTGGACGGACGAGTGCCAAGCACAGGACGTCC

Q   H   I   I   A   E   V   S   R   T   C   L   L   T   V   R   V   L   Q   A -

^cPLA2 starts here

CCCATCGCCTACCCTCTAAGGACC

121 ---------+---------+-----144

GGGTAGCGGATGGGAGATTCCTGGAT

H   R   L   P   S   K   D
```

This adapter was ligated with the largest BfaI-EcoRI fragment from clone 52A (bps 1630–4183) into EcoRI/XbaI digested pEDΔC vector. The resulted clone, named pEDΔC-n48, was confirmed to contain the desired inserts by restriction enzyme digestion and DNA sequencing. The sequence of the resulted clone is reported as SEQ ID NO:3.

Clone 52A was deposited with the American Type Culture Collection on Jan. 23, 1997 as accession number XXXXX. pEDΔC-n48 was deposited with the American Type Culture Collection on Jan. 22, 1997 as accession number YYYYY.

(2) Transfection and Activity Assay:

Eight micrograms of plasmid pEDΔC-n48 was transfected into COS-7 cells on 10 cm cell culture plate using lipofectamine (GIBCO BRL) according to manufacturer's protocol. PEDΔC vector DNA, pEMC-cPLA2, pEMCi-PLA2 were also transfected in parallel experiments. At 66 hours posttransfection, cells were washed twice with 10 ml of ice-cold TBS, scraped into 1 ml of TBS. Cell pellets were collected, resuspended in lysis buffer (10 mM HEPES, pH 7.5. 1 mM EDTA, 0.1 mM DTT, 0.34 M sucrose, 1 mM PMSF and 1 ug/ml leupeptin) and lysed in a Parr-bomb (700 psi, 10 min) on ice. The lysate were centrifuged at 100,000 g for 1 hr at 4° C. The supernatant (cytosolic fraction) was transferred to another set of tubes and the pellets were resuspended in 0.5 volume of lysis buffer (particulate fraction). Twenty ul of the lysate or cytosolic fraction or 10 ul of the particulate fraction were mixed on ice with 100 ul substrate containing 20 uM 1-palmitoyl-2-[1-14C]-arachidonyl-L-3-Phosphotidylcholine, 80 mM glycine, pH 9.0. 200 uM Triton-X 100, 70% glycerol and 10 mM CaCl2. The reaction was carried out at 37° C. for 15 min and the products analyzed as described (PNAS 87, pp7708–7712, 1990).

EXAMPLE 2

Phopholipase Assays 1. sn-2 Hydrolysis Assays

A) Liposome: The lipid, e.g. 1-palmitoyl-2-[$^{14}$C] arachidonyl-sn-glycero-3-phosphocholine(PAPC), 55 mCi/mmol, was dried under a stream of nitrogen and solubilized in ethanol. The assay buffer contained 100 mM Tris-HCl pH 7, 4 mM EDTA, 4 mM EGTA, 10% glycerol and 25 µM of labelled PAPC, where the volume of ethanol added was no more than 10% of the final assay volume. The reaction was incubated for 30 minutes at 37° C. and quenched by the addition of two volumes of heptane:isopropanol:0.5M sulfuric acid (105:20:1 v/v). Half of the organic was applied to a disposable silica gel column in a vacuum manifold positioned over a scintillation vial, and the free arachidonic was eluted by the addition of ethyl ether (1 ml). The level of radioactivity was measured by liquid scintillation.

Variations on this assay replace EDTA and EGTA with 10 mM CaCl$_2$.

B) Mixed Micelle Basic: The lipid was dried down as in (A) and to this was added the assay buffer consisting of 80 mM glycine pH 9, 5 mM CaCl$_2$ or 5 mM EDTA, 10% or 70% glycerol and 200 µM triton X-100. The mixture was then sonicated for 30–60 seconds at 4° C. to form mixed micelles.

C) Mixed Micelle Neutral: As for (B) except 100 mM Tris-HCl pH 7 was used instead of glycine as the buffer.

2. sn-1 Hydrolysis Assays

Sn-1 hydrolysis assays are performed as described above for sn-1 hydrolysis, but using phospholipids labelled at the sn-1 substituent, e.g. 1-[$^{14}$C]-palmitoyl-2-arachidonyl-sn-glycero-3-phophocholine.

Patent and literature references cited herein are incorporated by reference as if fully set forth.

What is claimed is:

1. A method for identifying an inhibitor of phospholipase activity, said method comprising:
    a) contacting a phospholipid with a candidate inhibitor compound and a phospholipase enzyme peptide, wherein the phospholipase enzyme peptide comprises an amino acid sequence selected from:
        i) the amino acid sequence of SEQ ID NO: 2;
        ii) a fragment of the amino acid sequence of SEQ ID NO: 2 having activity in a mixed micelle assay with 1-palmitoyl-2[$^{14}$C]-arachidonyl-phosphatidylcholine as a substrate;
        iii) the amino acid sequence of SEQ ID NO: 4; and
        iv) a fragment of the amino acid sequence of SEQ ID NO: 4 having activity in a mixed micelle assay with 1-palmitoyl-2[$^{14}$C]-arachidonyl-phosphatidylcholine as a substrate; and
    b) determining whether the phospholipase enzyme peptide cleaves the phospholipid and releases fatty acid, thereby identifying an inhibitor of phospholipase activity.

2. The method of claim 1, wherein the phospholipase enzyme peptide comprises the amino acid sequence of SEQ ID NO: 2.

3. The method of claim 1, wherein the phospholipase enzyme peptide comprises a fragment of the amino acid sequence of SEQ ID NO: 2 having activity in a mixed micelle assay with 1-palmitoyl-2[$^{14}$C]-arachidonyl-phosphatidylcholine as a substrate.

4. The method of claim 1, wherein the phospholipase enzyme peptide comprises the amino acid sequence of SEQ ID NO: 4.

5. The method of claim 1, wherein the phospholipase enzyme peptide comprises a fragment of the amino acid sequence of SEQ ID NO: 4 having activity in a mixed micelle assay with 1-palmitoyl-2[$^{14}$C]-arachidonyl-phosphatidylcholine as a substrate.

6. A method for identifying an inhibitor of phospholipase activity, said method comprising:
    a) contacting a phospholipid with a candidate inhibitor compound and a phospholipase enzyme peptide, wherein the phospholipase enzyme peptide comprises an amino acid sequence selected from:
        i) the amino acid sequence of SEQ ID NO: 2;
        ii) a fragment of the amino acid sequence of SEQ ID NO: 2 having activity in a mixed micelle assay wish 1-palmitoyl-2[$^{14}$C]-arachidonyl-phosphatidylcholine as a substrate;

iii) the amino acid sequence of SEQ ID NO: 4; and
iv) a fragment of the amino acid sequence of SEQ ID NO: 4 having activity in a mixed micelle assay with 1-palmitoyl-2-[$^{14}$C]-arachidonyl-phosphatidylcholine as a substrate; and b) determining whether the phospholipase enzyme peptide activity is inhibited by the candidate inhibitor compound, thereby identifying an inhibitor of phospholipase activity.

7. The method of claim 6, wherein the phospholipase enzyme peptide comprises the amino acid sequence of SEQ ID NO: 2.

8. The method of claim 6, wherein the phospholipase enzyme peptide comprises a fragment of the amino acid sequence of SEQ ID NO: 2 having activity in a mixed micelle assay with 1-palmitoyl-2-[$^{14}$C]-arachidonyl-phosphatidylcholine as a substrate.

9. The method of claim 6, wherein the phospholipase enzyme peptide comprises the amino acid sequence of SEQ ID NO: 4.

10. The method of claim 6, wherein the phospholipase enzyme peptide comprises a fragment of the amino acid sequence of SEQ ID NO: 4 having activity in a mixed micelle assay with 1-palmitoyl-2-[$^{14}$C]-arachidonyl-phosphatidylcholine as a substrate.

11. A method for identifying an inhibitor of phospholipase activity, said method comprising:

a) contacting a phospholipid with a candidate inhibitor compound and a phospholipase enzyme peptide, wherein the phospholipase enzyme peptide comprises an amino acid sequence encoded by a polynucleotide that hybridizes to the nucleic acid sequence set forth in SEQ ID NO: 1 under stringent conditions of 4×SSC at 65 degrees C.; and b) determining whether the phospholipase enzyme peptide activity is inhibited by the candidate inhibitor, thereby identifying an inhibitor of phospholipase activity.

12. A method for identifying an inhibitor of phospholipase activity, said method comprising:

a) contacting a phospholipid with a candidate inhibitor compound and a phospholipase enzyme peptide, wherein the phospholipase enzyme peptide comprises an amino acid sequence encoded by a polynucleotide that hybridizes to the nucleic acid sequence set forth in SEQ ID NO: 3 under stringent conditions of 4×SSC at 65 degrees C.; and b) determining whether the phospholipase enzyme peptide activity is inhibited by the candidate inhibitor, thereby identifying an inhibitor of phospholipase activity.

13. The method of any one of claims 1–12, further comprising forming a composition comprising the inhibitor and a pharmaceutically acceptable carrier.

* * * * *